(12) United States Patent
Couaraze et al.

(10) Patent No.: US 8,337,892 B1
(45) Date of Patent: Dec. 25, 2012

(54) LOW-DOSE TABLETS AND PREPARATION METHOD

(75) Inventors: Guy Couaraze, Les Clayes-sous-Bois (FR); Bernard Leclerc, Igny (FR); Pierre Tchoreloff, Bures-sur-Yvette (FR); Patrick Sanial, Morainvilliers (FR)

(73) Assignee: ETHYPHARM, Houdan (FR)

( * ) Notice: Subject to any disclaimer, the term of this patent is extended or adjusted under 35 U.S.C. 154(b) by 2028 days.

(21) Appl. No.: 10/031,949

(22) PCT Filed: Jul. 25, 2000

(86) PCT No.: PCT/FR00/02132
§ 371 (c)(1), (2), (4) Date: May 1, 2002

(87) PCT Pub. No.: WO01/06982
PCT Pub. Date: Feb. 1, 2001

(30) Foreign Application Priority Data

Jul. 26, 1999 (FR) ..................... 99 09653

(51) Int. Cl.
*A61K 9/20* (2006.01)
*A61K 9/36* (2006.01)
*A61K 9/28* (2006.01)

(52) U.S. Cl. ........ 424/480; 424/464; 424/465; 424/474; 424/479; 514/960; 514/961

(58) Field of Classification Search .................. 424/489, 424/490, 493, 464, 465, 474, 479, 480; 514/960, 514/961
See application file for complete search history.

(56) References Cited

U.S. PATENT DOCUMENTS

| | | | | |
|---|---|---|---|---|
| 2,996,431 A | * | 8/1961 | Barry | 424/10.3 |
| 4,489,026 A | * | 12/1984 | Yalkowsky | 264/123 |
| 4,634,587 A | * | 1/1987 | Hsiao | 424/495 |
| 4,684,516 A | * | 8/1987 | Bhutani | 424/469 |
| 4,806,361 A | * | 2/1989 | Harrison et al. | 424/495 |
| 4,925,674 A | * | 5/1990 | Giannini et al. | |
| 4,966,770 A | * | 10/1990 | Giannini et al. | 424/461 |
| 4,983,399 A | * | 1/1991 | Maish | 424/465 |
| 5,026,560 A | * | 6/1991 | Makino et al. | 424/494 |
| 7,829,122 B2 | * | 11/2010 | Bruna et al. | 424/490 |

FOREIGN PATENT DOCUMENTS

| | | |
|---|---|---|
| EP | 0 361 874 | 4/1990 |
| WO | WO 8802629 A1 * | 4/1988 |
| WO | WO 97/25028 | 7/1997 |
| WO | WO 98/10762 | 3/1998 |

OTHER PUBLICATIONS

Rudnic, Edward and Schwartz, Joseph, Oral Solid Dosage Forms, 1990, Remington's Pharmaceutical Sciences, 18th Edition, pp. 1635-1636.*

Search Report issued Mar. 24, 2000 in corresponding FR Appln 2796840.

* cited by examiner

*Primary Examiner* — John Pak
*Assistant Examiner* — Andriae M Holt
(74) *Attorney, Agent, or Firm* — RatnerPrestia

(57) ABSTRACT

The invention concerns a microgranule tablet comprising a low dose of active principle containing a directly compressible diluent. The invention is characterized in that the directly compressible diluent consists exclusively of neutral microgranules, and the active principle is set on the neutral microgranules and is not coated with an agent designed to modify its release or mask its taste.

3 Claims, No Drawings

LOW-DOSE TABLETS AND PREPARATION METHOD

The present invention relates to pharmaceutical tablets comprising low doses of active principle.

Dosing nonhomogeneity within tablets is one of the major problems encountered in the formulation of compositions comprising a low dose of an active principle. For active principles with a low therapeutic margin, underdosing leads to therapeutic ineffectiveness and overdosing can result in toxic side effects.

Tablets are composed of one or more active principles and of tableting excipients, such as diluents, binders, lubricants and disintegrating agents. The active principle and the excipients are generally provided in the form of powders which are subjected to tableting, with or without preliminary treatment.

The various processes for the manufacture of tablets, namely dry granulation, direct compression and wet granulation, are presented in "Remington's Pharmaceutical Sciences, 16th Ed., 1980, Mack Publ. Co. of Easton, Pa., USA, pp. 1553-1576".

Dry granulation is reserved for specific types of production, such as the manufacture of tablets comprising active principles which are soluble in water or sensitive to heat and to moisture. This technique is poorly suited to low doses of active principles because of the difficulty of obtaining homogeneous blends of dry powders.

Direction compression does not comprise a granulation stage prior to the compression and makes possible a considerable saving in time. Given that the majority of active principles have poor compressibility and/or are used in a low amount per unit dose, they have to be blended with excipients which are directly compressible and which are compatible with the active principle in order to be able to be subjected to direct compression.

Direct compression is carried out on high speed rotary machines. The feed device, which generally operates by gravity, is very sensitive to the agglomeration of the powders or to the setting solid thereof. The rheology of the blend of powders to be tableted is therefore a determining factor in guaranteeing the uniformity in weight of the tablets and the uniformity of their contents.

Another major disadvantage of the direct compression technique arises from the risk of separation of the powders or "demixing". This demixing leads to tablets which are nonhomogeneous in composition.

Thus, using the direct compression technique, it is possible to observe a poor distribution of the active principle in the excipients and a separation of the active principle and the excipients during the blending operation and in particular during all the transfer operations, leading to a variation in weight and in the content of active principle of the tablets. The poor fluidity of the blend of powders generally is an aggravating factor. The separation of the active principle and excipients in the blend of powders before tableting is observed in particular when the active principle and excipients differ greatly in particle size.

Like dry granulation, direct compression is therefore poorly suited to tablets comprising low doses of active principle.

Furthermore, direct compression is not always desirable, in particular when the active principle is toxic: it is preferable to reduce the emission of dust by agglomerating the constituents by wet granulation.

Wet granulation consists in spraying a binder in solution onto the powdered active principle(s)/excipient(s) blend and in then granulating the wet blend. Wet granulation has many advantages.

The formation of the grains limits the risks of segregation of the powders composed of particles with different sizes and shapes: there is therefore greater assurance that the final tablet will be homogeneous throughout its bulk. Furthermore, the conversion of a powder into grains makes it possible to reduce the problems of dust. The flow of the blend in the tableting chamber is facilitated, which ensures that the weight of the tablets will be uniform. Finally, rendering the powder more dense makes possible easier subsequent tableting.

However, migration of the active principle inside the granule can take place during the drying stage. This phenomenon of migration is reinforced when the active principle is soluble in the granulation excipient. Another problem arises for crystalline active principles exhibiting a degree of polymorphism. Complete or partial dissolution of the active principle during the granulation, followed by precipitation during the drying, changes the particle sizes of the active principle and optionally its crystallographic state. Such modifications have a direct influence on the dissolution and the bioavailability of the active principle.

A number of approaches have been provided in the prior art for solving the problem of the nonhomogeneity of tablets comprising low doses of active principle, such as combining, with a given active principle, a specific blend of excipients which makes it possible to prevent demixings, micronizing the active principle or alternatively atomizing it or agglomerating it with the direct compression excipient.

U.S. Pat. No. 3,568,828 provides the dissolution of a blend of estrogen and progesterone in chloroform using wet granulation. The process consists subsequently in spraying the solution onto microcrystalline cellulose, in drying the blend, in adding lactose and a lubricant to the blend, and in then tableting the combined mixture. The use of volatile solvents represents a major disadvantage, for reasons of safety of manufacture and of residual amounts in the tablets.

U.S. Pat. No. 4,489,026 provides tablets comprising less than 10 micrograms of active principle per tablet. These tablets are obtained by very slowly spraying the solution of active principle in a volatile solvent onto a very finely divided powder of a highly absorbent excipient which is insoluble in the solvent. The excipient is chosen from lactose, starch, calcium carbonate, $TiO_2$ and microcrystalline cellulose. The process disclosed in this document is slow and employs volatile solvents.

Thiel et al. (J. Pharm. Pharmacol., 1986, 38, 335-343) have provided the use of the fluidized air bed granulation technique. The active principle is micronized and blended with the powdered excipients. The blend is subjected, in the fluidized air bed device, to spraying with a solution of binder.

Michael et al. (Pharmaceutical Technology, June 1988, pp. 68-84) have disclosed a process which consists in spraying an aqueous solution of PVP onto an excipient with a relatively large particle size, for example lactose. The active principle, with a low particle size, is subsequently sprayed and adheres to the surface of the moistened particles of excipient. Problems related to the drying and to the poor fluidity of the active principle remain.

WO 97/04750 discloses a process which consists in adding, in a granulator, a 1% aqueous solution of active principle to a directly compressible excipient which is preferably soluble in the solution. The water evaporates without heating under the effect of a stream of air. The granules are subsequently tabletted. This process is limited to water-soluble active principles.

Few documents of the prior art disclose the preparation by direct compression of low dose tablets.

EP 503 521 provides the blending of very fine particles of active principle with a small amount of excipients and then the gradual addition of the remainder of the excipients. This method is based on the electrostatic adhesion of the fine particles of active principle to the larger particles of excipients. This very lengthy method only applies to certain active principles and is highly dependent on the surface condition of the particles of active principle and of the excipients.

The tablets disclosed in EP 503 521 comprise a micronized steroid and an atomized polyol, such as lactose, mannitol, sorbitol, cellulose, xylitol, dextrose, fructose or sucrose, preferably lactose. Each mg tablet comprises 180 micrograms of active principle. The variation in the content of active principle is less than 0.5%.

Greaves F. C. et al. (Pharmaceutical Technology, January 1995, pp. 60-63) and WO 95/17169 disclose tablets obtained by direct compression which comprise less than 10 mg of micronized estradiol. The estradiol is combined with agglomerated (and nonatomized) mannitol, with microcrystalline cellulose and with croscarmellose sodium.

In the context of the present invention, the Applicant Company has succeeded in developing a tablet obtained by direct compression of neutral microgranules.

This is because the Applicant Company has discovered that neutral microgranules were directly compressible.

An excipient, in order to be used in direct compression, must have good flowability, must not spontaneously agglomerate, must form a tablet with good mechanical or cohesive strength under the effect of a reasonable compression force and must make possible disintegration in an appropriate time. Numerous directly compressible diluents and binders have been developed. Excipients for direct compression remain expensive as they require elaborate preparation processes or the addition of numerous additives.

Sugars and carbohydrates are commonly used as binders and disintegrating agents in the formulation of tablets because of their pleasant taste. However, they are in a crystalline form and do not always exhibit good direct compression properties, and the powders which result therefrom are not very fluid, with the result that they have to be subjected to a surface treatment or be used in combination with specific additives in order to be directly compressible.

Directly compressible lactose is one of the most widely used excipients in direct compression: however, it is incompatible with some active principles.

Directly compressible starch (or pregelatinized starch) is subjected to a chemical and mechanical treatment in order to prevent aggregation of the starch grains. It is composed of 5% amylose, 15% amylopectin and 80% unmodified starch. It is used as binder (in the form of a solution), as diluent or as disintegrating agent.

Directly compressible sucrose comprises between 95 and 98% of sucrose and an additive such as starch, maltodextrin, inverted sugar or a lubricant. It is used as binder and in particular as diluent.

Other direct compression excipients include mannitol, microcrystalline cellulose and dicalcium phosphate. Direct compression granules exhibiting good fluidity based on fructose, lactitol or xylitol have also been developed; they are prepared by atomization or by agglomeration.

In the prior art, neutral microgranules are used for attaching a coating of active principle and are generally coated with a polymer film intended to modify the release of the active principle.

The United States Pharmacopoeia (USP XVII, 1990) describes neutral microgranules as essentially spherical granules comprising between 62.5 and 91.5% of sucrose, the remainder being composed essentially of starch. The United States Pharmacopoeia also requires a distribution in the size of the particles such that the variation with respect to the indicated range (for example 425-500, 500-600, 710-850 or 1000-1400 microns) is low and such that the diameter of the neutral microgranules is therefore uniform. The solubility of the neutral microgranules varies according to their sucrose content. They are prepared by coating crystalline sucrose with a suspension of starch in sugar syrup. Generally, the greater the diameter of the neutral microgranules, the greater the proportion of starch. Neutral microgranules with a size of between 200 μm and 2000 μm can be obtained commercially.

In the prior art, numerous tableting studies have been carried out on uncoated inert granules but no study has been carried out on neutral microgranules.

The study of the tableting of nuclei prepared by extrusion/spheronization starting from microcrystalline cellulose, lactose or dicalcium phosphate reveals that microcrystalline cellulose is a plastic material, that lactose knits together by fragmentation and then by plastic deformation, and that dicalcium phosphate dihydrate knits together essentially by fragmentation. Microcrystalline cellulose powder is known as being highly compressible but this study shows that microcrystalline cellulose nuclei obtained by extrusion/spheronization are not compressible and give soft tablets. Nuclei comprising a blend of microcrystalline cellulose and lactose are more compressible and more brittle than microcrystalline cellulose nuclei. Finally, nuclei comprising a blend of dicalcium phosphate dihydrate and microcrystalline cellulose are more easily subjected to plastic deformations than the two other types of nuclei; they have a higher level of cohesion and are more compressible (Schwartz J B., Nguyen N H. and Schnaare R L., Compaction Studies on Beads: Compression and Consolidation Parameters, Drug Dev. Ind. Pharm., 1994, 20 (20), 3105-3129).

Similar results have been obtained with lactose/microcrystalline cellulose nuclei (Wang C. et al., Drug Dev. Ind. Pharm., 1995, 21(7), 753-779). This is because these nuclei have different compression and consolidation properties from those of powders with the same composition. The low compressibility of nuclei rich in microcrystalline cellulose has been attributed to the loss in plasticity of the cellulose during the granulation process.

The properties of granules comprising a dicalcium phosphate/microcrystalline cellulose (80/20) blend have also been studied (Johannson B., Nicklasson F. and Alderborn G., Tabletting properties of pellets of varying porosity consisting of dicalcium phosphate and microcrystalline cellulose, Pharm. Res., 1995, 12 (9), S-164).

The mechanism of compression of nuclei comprising microcrystalline cellulose, alone or as a mixture with 10% of lactose, of propanolol or of dicalcium phosphate, has been compared with that of the corresponding powders. At equal porosities, the nuclei require a lower compression pressure than the corresponding powders. The compressibility of microcrystalline cellulose decreases by addition of lactose, of dicalcium phosphate or of propanolol (Maganti L. and Celik M., Compaction studies on pellets, I. Uncoated pellets, Int. J. Pharm., 1993, 95, 29-42; Celik M., Compaction of multiparticulate oral dosage forms, in Multiparticulate Oral Drug Delivery, New York, Marcel Dekker, 1994, 181-215).

Microcrystalline cellulose nuclei comprising theophylline have been prepared by extrusion/spheronization using a variable proportion of a water/ethanol mixture. The water results in harder and less porous grains which are therefore less compressible. The grains prepared with ethanol are more brittle, break during tableting and form new surfaces for bonding (Millili G P. and Schwartz J B., The strength of microcrystalline cellulose pellets, The effects of granulating with water ethanol mixtures, Drug Dev. Ind. Pharm., 1990, 16(8), 1411-1426).

It emerges from all the studies carried out on granules formed from inert excipients that the tableting properties of the nuclei are very different from those of the powders and that it is therefore impossible to predict the behavior of the nuclei in tableting from the mechanical properties of the powders used for their preparation.

In the context of the present invention, the Applicant Company has developed a pharmaceutical tablet comprising a low dose of active principle.

WO 97/25028, U.S. Pat. No. 4,684,516, EP 361 874 and WO 98/10762 disclose tablets comprising low doses of active principle in which the active principle formulated in modified-release granules. These granules are composed of a neutral nucleus coated with a layer comprising the active principle and then with a polymer layer intended to slow down the release of the active principle.

This polymer layer confers, on the granules, a compressibility and a tableting behavior which are entirely different from those of neutral granules coated with a single layer of active principle. The teaching of these documents therefore cannot be applied to tablets formed from granules comprising low doses of active principle in which the active principle is uncoated.

A subject matter of the present invention is a tablet comprising a low dose of active principle formed from microgranules comprising a directly compressible diluent, characterized in that the directly compressible diluent is composed solely of neutral microgranules and in that the active principle is attached as a coating to the neutral microgranules and is not coated with an agent intended to modify its release or to mask its taste.

In the context of the present invention, the term "neutral microgranules" is understood to mean essentially spherical granules comprising sucrose and starch. Neutral microgranules particularly valued in the context of the invention comprise less than 91.5% of sucrose.

The microgranules present in the tablets of the invention are composed of a neutral microgranule to which the active principle is attached as a coating. Given that the tablets are low dose ones, it is not necessary to add excipients during the attaching of the coating of the active principle. The microgranules are preferably composed of a neutral microgranule, at the surface of which the active principle is adsorbed.

If, despite everything, excipients prove to be preferable in carrying out the attaching of the coating of the active principle, the choice of their composition and of their proportion will be such that they do not substantially modify the tableting properties of the neutral microgranules.

The present invention advantageously employs spherical particles, guaranteeing good flowability and good homogeneity of the blend to be tableted.

The excellent rheological properties of the neutral microgranules make them good candidates as direct compression excipient. The flow time of the neutral microgranules under the conditions of the test described in the Pharmacopoeia is much less than 10 seconds. This property makes possible very efficient feeding of the tablet presses. In addition, the neutral microgranules have a very low compaction volume.

The neutral microgranules have the advantage of constituting a direct compression excipient which does not generate dust.

Finally, the neutral microgranules have a disintegration time much less than 15 minutes.

In addition, the present invention makes it possible to avoid the problems of demixing generally observed in direct compression as all the particles to be tableted have the same size.

The dimension or the mass of the tablets can be adjusted as desired for low dosages since the demixing problems (which limit these parameters in conventional processes) are eliminated. Furthermore, the shape, the ability to be scored and the engraving of the tablets are retained when such systems are used.

Finally, the tablet according to the invention can advantageously be used as placebo tablet, in particular during technical trials, such as the operational qualification of tableting equipment, performance qualification, machine trials after format change and machine adjustment validation.

The neutral microgranules have a size of between 100 and 2000 µm, preferably between 200 and 600 µm, or preferably between 200 and 400 µm.

The tablets of the present invention exhibit a uniformity in mass of much less than 5% and of the order of 1% for tablets with a mass of the order of 300 to 500 mg, a friability of less than 1%, a disintegration time at 37° C. of less than 15 minutes, and a hardness of the order of 0 to 20 daN. These parameters can be adjusted by the interplay of the tableting parameters.

The tablet is preferably composed of an active principle attached as a coat to neutral microgranules and of tableting excipients in an amount of less than 1% by weight with respect to the weight of the tablet.

The tablet can additionally comprise a lubricant in an amount of less than 1% by mass, preferably of between 0.125 and 0.75% by mass, more preferably of the order of 0.25% to 0.5% by mass, of the tablet.

The lubricant makes it possible to reduce friction between particles and between particles and the press mold. It also makes it possible to reduce adhesion of the grains to the punches and to obtain a degree of gloss. The lubricant is chosen, for example, from magnesium, zinc or calcium stearate, talc, Aerosil®, stearic acid and PEGs.

The active principle is advantageously chosen from steroids, neuroleptics and other active principles which act on the central nervous system, agents for protecting the cardiovascular system, hormones or homeopathic active principles.

The amount of active principle is preferably less than 40 mg/g, more preferably less than 10 mg/g, of system to be tableted, to be adjusted according to the type of active principle, the method of attaching the coating and its effect after attaching the coating on the mechanical properties of the system which is ready to be tableted.

The attaching of the coating of the active principle to the neutral microgranules is carried out according to conventional methods, such as the attaching of a coating starting from solutions or suspensions, in a pan or in a fluidized air bed, optionally in the presence of binding agents in the spraying solvent. The amount of binder will be adjusted according to the nature and the amount of active principle to be attached as a coating.

The solvent used for the attaching of the coating will generally be water or any other authorized solvent with an appropriate drying stage.

The tablets according to the invention can be film coated, either to improve their appearance or to mask the color or to protect the active principle from light, moisture or oxygen in the air.

The tablets according to the invention can also be coated with a gastroresistant film or a film intended for the modified release of the active principle.

Another subject matter of the present invention is a tableting premix which consists of a composition containing between 99 and 100% by mass of neutral microgranules coated with active principle and between 0 and 1% by mass of a lubricant, which composition is intended to be subjected to direct compression.

The active principle preferably represents less than 4% by mass of the neutral microgranules.

Finally, the present invention relates to a process for the preparation of the tablets of the invention. According to this process, the compression force is advantageously between 5 and 50 kN when the compression surface area is 1 cm² (i.e. 50 to 500 MPa), preferably between 10 and 30 kN.

The present invention is illustrated without implied limitation by the following examples.

EXAMPLE 1

Properties on Tableting on an Alternating Press of the Neutral Microgranules without the Attachment of a Coating The neutral microgranules are obtained from NP-Pharm.
The properties are studied on three batches A (500-600 µm), B (200-250 µm) and C (250-300 µm). Batch A is studied at two lubrication levels: 0.25% (A1) and 0.5% (A2) of magnesium stearate. Batches B and C are studied at a degree of lubrication of 0.25%. 100 g of neutral microgranules of each batch are weighed out and, depending upon the level of magnesium stearate, 0.25 g or 0.50 g of lubricant is added. Blending is carried out on a Turbula (48 rpm) for one minute.

Each batch is tested at 3 different levels of compression forces of the order of: 10, 15 and 20 kN, on an alternating tablet press (Frogerais OA; punches 1 cm²; mold height standardized at 1 cm, i.e. a working volume of 1 cm³).

These various systems are tested on an alternating tablet press equipped with force sensors (strain gauges) and inductive displacement sensors on the upper and lower punches. The tablets obtained are subjected to a test of hardness by diametrical compression with a maximum force of 20 daN (Schleuniger type).

During tableting, the forces are measured at the two punches. The upper punch force (UPF) is converted into pressure (MPa) by taking into account the surface area of the punch. The ratio of the lower punch force/upper punch force gives the percentage of transmission.

During the decompression phase, the compact passes through a sudden stage of expansion related to the elastic recovery, possibly followed by viscoelastic behavior during ejection. This stage can be studied by virtue of two parameters: the residual force and the ejection force. The monitoring of this stage also makes it possible to describe the problems of adhesion to the mechanical components.

The residual force is measured at the lower punch when the stress exerted at the upper punch has ceased and when ejection has not yet been carried out. An optimum for good conditions for tableting of the neutral microgranules is obtained for a value of less than 25 daN.

The ejection force corresponds to the force necessary for the ejection of the tablet out of the mold by the lower punch. In order not to have problems during the tableting operation, it is commonly accepted that this force must be less than or of the order of 50 daN.

Likewise, the cohesion index, equal to:

$$I_c = \frac{\text{Hardness }(daN)}{\text{Compression force }(daN)} \times 10^5$$

is calculated.

The mass and thickness of the tablets are also measured. The results obtained are presented in Table 1.

TABLE 1

| Batch | Order of magnitude of the force applied (kN) | Max. UPF (MPa) | Percentage of transmission (%) | Ejection force (daN) | Residual force (daN) | Hardness (daN) | Thickness (mm) | Mass (mg) | Cohesion index |
|---|---|---|---|---|---|---|---|---|---|
| A2 | 10 | 92.9 | 92.98 | 21.1 | 5.5 | 2.75 | 6.29 | 813.4 | 285 |
|    | 15 | 168.7 | 93.82 | 36.3 | 8.4 | 6.00 | 6.00 | 804.5 | 353 |
|    | 20 | 204.3 | 93.88 | 46.8 | 11.1 | 7.2 | 7.2 | 818.3 | 351 |
| A1 | 10 | 100.9 | 93.47 | 21 | 4.8 | 2.7 | 6.32 | 827.2 | 263 |
|    | 15 | 138.2 | 93.38 | 28 | 6.7 | 5.2 | 6.10 | 826.4 | 376 |
|    | 20 | 179.4 | 94.00 | 37 | 7.3 | 7.6 | 5.86 | 818.6 | 421 |
| B  | 10 | 111.4 | 95.65 | 24.9 | 6 | 9 | 6.05 | 810.1 | 806 |
|    | 15 | 158.5 | 94.72 | 33 | 6.5 | 13.8 | 5.84 | 813.7 | 875 |
|    | 20 | 211.8 | 95.09 | 44 | 7.4 | $\geq$20 | 5.65 | 812.1 | 1000* |
| C  | 10 | 118.9 | 92.66 | 20.4 | 8.9 | 7.77 | 6.06 | 832.4 | 652 |
|    | 15 | 158.8 | 95.20 | 26 | 4.9 | 12.7 | 5.78 | 820.1 | 807 |
|    | 20 | 217.2 | 95.08 | 34 | 5.7 | 18 | 5.74 | 827.9 | 830 |

*calculated on the basis of a hardness value of 20 daN.

The preceding results make it possible to study the properties of the neutral microgranules without an attached coating as a function of their size and of the degree of lubrication.

Comparison between 500-600 µm neutral microgranules (batch A) lubricated with 0.5% (batch A2) and 0.25% (batch A1) of magnesium stearate.

The influence of the level of magnesium stearate is important to evaluate as it can affect the dissolution and the release of the active principle (hydrophobic characteristics of the lubricant).

For 500-600 µm neutral microgranules, the difference in the hardnesses, when 0.25% or 0.5% of magnesium stearate is used, is very slight.

The percentage of transmission, also known as "lubricating index", remains very high for both systems, in the vicinity of 93%.

Finally, the ratio of upper punch force (UPF) to ejection force changes linearly with a coefficient of correlation of 0.99 and therefore allows it to be estimated (by extrapolation) that the acceptable limit for the ejection force of 50 daN will be reached for the two batches A1 and A2 between 230-260 MPa.

On the basis of these results, it appears that a level of magnesium stearate of 0.25% is sufficient.

Comparison between the neutral microgranules of different sizes (batches A1, B and C) with lubrication with 0.25% of magnesium stearate.

The hardness decreases very substantially when the size of the microgranules increases. At identical levels of increasing force, the hardness increases faster with the smaller systems.

The ejection force is lowest for batch C. The two other batches A1 and B are virtually identical, with a slightly higher ejection force. The limit of acceptability of 50 daN would be reached in the vicinity of an applied pressure of 250 MPa for A1 and B and would exceed 300 MPa for C (evaluation by extrapolation).

It is clearly seen that the cohesion index decreases with the increase in the size of the microgranules. The optimum cohesion index for direct compression is in the vicinity of 1 000; this value is achieved or virtually achieved for the small neutral microgranules tested (batch B).

The active principle is molsidomine, attached as a coating to the neutral microgranules starting from an aqueous solution or in the presence of a binder in solution, Pharmacoat 603, according to the quantitative ratios given in the following table:

| BATCH | DEGREE OF ATTACHMENT OF COATING | % OF BINDER |
|---|---|---|
| Ma | 6.3 mg/g | — |
| Mb | 11.4 mg/g | — |
| Mc | 5.9 mg/g | 0.14% |
| Md | 11.2 mg/g | 0.27% |

The operation is carried out as in Example 1 and the batches are listed at three levels of compression force between 7.5 and 26 kN (i.e. between 75 and 260 MPa, expressed as stress).

The tablets are subjected to a hardness test as in Example 1; their mass is also measured. The results are presented in Table 2

TABLE 2

| BATCH | Order of magnitude of the Applied Force (kN) | Max. UPF (MPa) | Percentage of transmission | Ejection force (daN) | Residual force (daN) | Hardness (daN) | Mass (mg) | Cohesion index |
|---|---|---|---|---|---|---|---|---|
| Neutral micro- | 7 | 75 ± 2 | 93.4 ± 0.4 | 17 ± 1 | 5.3 ± 0.5 | 5.8 ± 0.4 | 839 ± 11 | 776 ± 39 |
| granules | 12 | 120 ± 2 | 94.5 ± 0.1 | 24 ± 1 | 8.0 ± 0.0 | 11.0 ± 0.3 | 842 ± 2 | 900 ± 24 |
| (200-300 µm) | 18 | 175 ± 3 | 94.8 ± 0.1 | 32 ± 2 | 8.6 ± 0.5 | 17.3 ± 0.7 | 840 ± 1 | 988 ± 34 |
| Ma | 18 | 173 ± 7 | 94.3 +0.2 | 45 ± 2 | 8.2 ± 0.6 | 6.4 ± 0.3 | 783 ± 5 | 370 ± 11 |
|  | 25 | 240 ± 12 | 94.9 ± 0.3 | 59 ± 5 | 11.6 ± 0.8 | 10.2 ± 0.5 | 795 ± 5 | 425 ± 14 |
|  | 28 | 272 ± 10 | 94.6 ± 0.1 | 73 ± 7 | 15.0 ± 0.0 | 10.9 ± 0.4 | 804 ± 4 | 402 ± 17 |
| Mb | 15 | 152 ± 13 | 94.1 ± 0.2 | 40 ± 4 | 9 ± 1 | 7 ± 1 | 806 ± 10 | 448 ± 26 |
|  | 20 | 205 ± 18 | 94.2 ± 0.2 | 54 ± 5 | 12 ± 1 | 10 ± 1 | 813 ± 11 | 480 ± 32 |
|  | 26 | 262 ± 11 | 94.3 ± 0.1 | 71 ± 3 | 16 ± 1 | 13.0 ± 0.6 | 819 ± 5 | 495 ± 16 |
| Mc | 14 | 138 ± 8 | 94.8 ± 0.2 | 32 ± 3 | 2 ± 2 | 5.7 ± 0.5 | 755 ± 6 | 416 ± 20 |
|  | 20 | 205 ± 8 | 95.2 ± 0.2 | 47 ± 3 | 11 ± 1 | 12.0 ± 0.8 | 765 ± 4 | 585 ± 30 |
|  | 25 | 255 ± 6 | 95.5 ± 0.2 | 60 ± 2 | 12 ± 0 | 14.2 ± 0.8 | 759 ± 2 | 557 ± 25 |
| Md | 11 | 111 ± 2 | 94.4 ± 0.2 | 26.7 ± 0.8 | 4.6 ± 0.5 | 5.0 ± 0.2 | 756 ± 2 | 453 ± 17 |
|  | 17 | 175 ± 5 | 94.8 ± 0.1 | 41 ± 2 | 8.0 ± 0.0 | 9.0 ± 0.4 | 769 ± 3 | 512 ± 21 |
|  | 25 | 252 ± 6 | 95.0 ± 0.2 | 58 ± 4 | 10.7 ± 0.8 | 15.0 ± 0.5 | 778 ± 2 | 594 ± 19 |

Conclusion

For the system of the 500-600 µm neutral microgranules, the degree of lubrication of 0.25% appears sufficient to produce sufficient tabletability with a satisfactory range of hardness. The limit of tabletability relating to the ejection force would be reached in the vicinity of a compression pressure of 230-260 MPa. The transmission ratio, always greater than 90%, is excellent in all these scenarios.

The compressibility increases as the size of the microgranules decreases. The cohesion index of approximately 1000 (regarded as value of excellence) is virtually achieved with microgranules of approximately 200-300 µm. The cohesive properties of the small- to intermediate-sized systems without the attachment of a coating are nevertheless very good.

EXAMPLE 2

Properties on Tableting of the Neutral Microgranules which have Attached a Coating of Molsidomine on an Instrument-Controlled Alternating Tablet Press The following batches of neutral microgranules with an attached coating are prepared by using neutral microgranules with a particle size of between 200 and 300 µm. The degree of lubrication is set at 0.25%.

The tablets obtained from neutral microgranules with an attached coating of AP are compared with the tablets obtained from the same neutral microgranules (same size) but not with an attached coating of active principle. These tests therefore make it possible to study the influence of the attaching to the neutral microgranules of a coating of molsidomine on their properties on tableting.

The neutral microgranules without the attachment of a coating give the same results as described in example 1 for the systems with a similar particle size.

The hardnesses obtained are satisfactory for relatively weak compression forces (75 MPa) and they increase rapidly when the compression force increases. High hardnesses of 17 daN are obtained for compression forces which are still relatively weak, of the order of 18 kN, i.e. 180 MPa. The cohesion indices tend towards excellence at values of the order of 900.

For the systems with the attachment of a coating, the levels of hardness are lower at an identical compression force. However, these levels of hardness are highly satisfactory for compression forces of the order of 15 to 25 kN. The cohesion indices are lower than for the neutral microgranules without the attachment of a coating but remain at highly acceptable values of the order of 400 to 500. The influence of the amount of active principle attached as a coating is not very noticeable with regard to these systems. On the other hand, it is possible to see the influence of the process for the attachment of the coating, since the systems in which the coating is attached in the presence of a binder prove to be more cohesive than the systems in which the coating is attached starting from a simple solution.

In all cases, the residual forces after compression are very weak and always less than 15 daN for the compression forces tested.

The ejection forces are generally acceptable but tend toward the limit values of 50 to 60 daN when the compression forces increase to 25 kN.

No phenomenon of sticking, jamming or capping of the tablets formed is seen, however. A very slightly greater lubrication makes it possible to reduce the ejection forces at the highest pressures. The margin of maneuver, in the conventional formulation/manufacture interplay (product/press pair), remains very large here.

The transmission ratios are excellent in all cases, of the order of 93 to 95%.

The mass of the tablet is very stable, with a random variation about the mean of less than 1.5% in the worst of the cases.

Conclusion

The systems of neutral microgranules with an attached coating of active principle exhibit highly advantageous compression properties. The cohesion of these systems is very good, even if it is influenced by the presence of the active principle attached as a coating at the surface of the neutral microgranules.

The force transmission and the uniformity of the masses are two major advantages of these systems.

EXAMPLE 3

Properties of the Neutral Microgranules without an Attached Coating on a Rotary Press as a Function of the Degree of Lubricant This test consists of the tableting on a rotary tablet press of neutral microgranules without an attached coating comprising different levels of magnesium stearate, in order to determine the minimum degree of lubricant necessary in order to obtain tablets with satisfactory characteristics.

The levels of magnesium stearate studied are 0.125, 0.25, 0.5 and 0.75%.

The size of the neutral microgranules is between 315 and 400 μm.

Preblending is carried out between half the mass of the microgranules and half the mass of stearate using a Turbula mixer for 1 minute.

The preblended part and the remainder of the microgranules and of the stearate are subsequently blended in an Erweka cube mixer for 5 minutes.

The volume of the mold is adjusted in order to obtain tablets of the order of 350 mg. The compression is adjusted in order for the hardness of the compacts to have an acceptable value for each content of stearate. The adjustment of the precompression is indexed at 4 and is unmodified.

After optimization of the adjustments of mass and of hardness, and after operating for 30 to 60 seconds, 20 tablets are removed every 30 seconds for 5 minutes.

The four parameters of hardness, mass, friability and disintegration time are subsequently measured.

Hardness: this test is intended to determine, under defined conditions, the resistance to breaking of the tablets, measured by the force necessary to bring about their breakage by diametrical compression.

It is measured using an Erweka device and is carried out on 10 tablets.

Mass: it is measured using a Sartorius balance and is carried out on 10 tablets.

Friability: this test is intended to determine, under defined conditions, the friability of the uncoated tablets, that is to say the phenomenon by which the surface of the tablets is damaged or exhibits signs of abrasion or of breakage under the effect of mechanical impacts or of attrition.

It is measured using an Erweka device and is carried out on 10 tablets.

Disintegration time: it is intended to determine the greater or lesser ability of the tablets to dissolve over time in a liquid medium. It is measured using an Erweka device and is carried out in water at 37° C. on 6 tablets.

The results obtained are presented in Tables 3 and 4.

TABLE 3

| Magnesium stearate (%) | Time (s) | 30 | 60 | 90 | 120 | 150 | 180 | 210 | 240 | 270 | 300 |
|---|---|---|---|---|---|---|---|---|---|---|---|
| 0.125 | Mass (mg) | 358.5 | 354.7 | 354.8 | 355 | 365 | 352.2 | 354.8 | 356.4 | 358.2 | 353.9 |
|  | Hardness (N) | 84.9 | 92.9 | 85.5 | 81.6 | 82.9 | 74.3 | 93.8 | 85.1 | 78.5 | 83.4 |
|  | Friability (%) | 0.85 | 0.22 | 0.14 | 0.1 | 0.12 | 0.12 | 0.10 | 0.15 | 0.20 | 0.19 |
| 0.25 | Mass (mg) | 357.5 | 357 | 355.7 | 350.5 | 361.7 | 353.9 | 360.3 | 352.9 | 361.5 | 357.5 |
|  | Hardness (N) | 87 | 83 | 82 | 88 | 82 | 89 | 85.3 | 81.8 | 83 | 88.6 |
|  | Friability (%) | 0.06 | 0.11 | 0.19 | 0.44 | 0.88 | 0.59 | 0.13 | 0.13 | 0.19 | 0.23 |
| 0.5 | Mass (mg) | 343.2 | 345.6 | 346.9 | 348.8 | 345.6 | 351 | 354.2 | 350.6 | 359.5 | 346.3 |
|  | Hardness (N) | 70.3 | 70.3 | 71.4 | 68.3 | 71.2 | 65.5 | 68.6 | 69.3 | 75.5 | 74.1 |
|  | Friability (%) | 0.158 | 0.176 | 0.179 | 0.098 | 0.088 | 0.135 | 0.014 | 0.131 | 0.115 | 0.138 |
| 0.75 | Mass (mg) | 349.3 | 345.5 | 354.7 | 351.4 | 352.1 | 351.4 | 345.8 | 351.4 | 350.8 | 353.7 |
|  | Hardness (N) | 59 | 59.5 | 56.8 | 56.1 | 56.9 | 60 | 58.4 | 56 | 61.1 | 59.9 |
|  | Friability (%) | 0.1 | 0.1 | 0.12 | 0.36 | 0.09 | 0.51 | 0.16 | 0.06 | 0.01 | 0.13 |

TABLE 4

| % of magnesium stearate | Disintegration time (minutes) |
|---|---|
| 0.125 | 8.8 |
| 0.25 | 9.5 |
| 0.50 | 11 |
| 0.75 | 22 |

Conclusion

Mass: The French Pharmacopoeia recommends a limit deviation as percentage of the mean mass of 5% for tablets corresponding to the mass involved. For the various levels of magnesium stearate, the values fluctuate on both sides of the mean and thus the distribution is random. All the batches are in accordance as the values found are much less than the limits set by the Pharmacopoeia.

Friability: according to the French Pharmacopoeia, the maximum loss in mass regarded as acceptable is 1% of the mass of the tablets subjected to the test. For the various levels of magnesium stearate used, we are aware that the results are much less than the standard of the Pharmacopoeia and thus the various batches are in accordance.

Hardness: the French Pharmacopoeia does not lay down a limit. For all the levels of magnesium stearate, the results show that we are always within the adjustment limits and therefore the various batches are in accordance.

Disintegration time: the French Pharmacopoeia sets disintegration conditions according to the type of tablet. For bare or uncoated tablets, the time must be less than 15 minutes. Our results are therefore in accordance with the standard of the Pharmacopoeia, except with 0.75% of magnesium stearate and with the compression force used, where the time is 22 minutes.

The tabletability of the neutral microgranules on a rotary tablet press is therefore demonstrated, with excellent results.

It should be noted that the production yields are excellent: the hopper empties without external help down to the last grains. The absence of production of dust in the press and the atmosphere throughout the operation is also very noticeable.

The invention claimed is:

1. A tablet consisting essentially of: coated neutral microgranules and an excipient, wherein:
   a) the neutral microgranules are spherical of uniform diameter from 100 to 2000 µm, and are directly compressible;
   b) the neutral microgranule coating consists essentially of a single layer of an active principle and optional binder, the optional binder being included in an amount of 0.27% by weight or less, wherein the active principle is less than 40 mg/g of the tablet, and said coating is free of any other agent modifying release of the active principle or masking its taste; and
   c) the excipient is a lubricant constituting less than 1% by weight of the tablet.

2. The tablet of claim 1, wherein the binder is a singular cellulosic material.

3. The tablet of claim 1, wherein the binder is hydroxypropylmethylcellulose.

* * * * *